(12) United States Patent
Larsson et al.

(10) Patent No.: US 7,998,697 B2
(45) Date of Patent: Aug. 16, 2011

(54) ENDOTOXIN ANALYSIS

(75) Inventors: Gen Larsson, Lidingö (SE); Per-Åke Nygren, Stockholm (SE)

(73) Assignee: Bioproduce Sthlm AB, Stockholm (SE)

( * ) Notice: Subject to any disclaimer, the term of this patent is extended or adjusted under 35 U.S.C. 154(b) by 493 days.

(21) Appl. No.: 12/092,451

(22) PCT Filed: Nov. 2, 2006

(86) PCT No.: PCT/SE2006/050448
§ 371 (c)(1),
(2), (4) Date: Oct. 7, 2008

(87) PCT Pub. No.: WO2007/053107
PCT Pub. Date: May 10, 2007

(65) Prior Publication Data
US 2009/0098590 A1    Apr. 16, 2009

(30) Foreign Application Priority Data
Nov. 2, 2005    (SE) ...................................... 0502426

(51) Int. Cl.
*C12Q 1/42*    (2006.01)
(52) U.S. Cl. ......................................... 435/23; 435/7.91
(58) Field of Classification Search ................... 435/23, 435/7.91
See application file for complete search history.

(56) References Cited

FOREIGN PATENT DOCUMENTS
WO    2004087942 A2    10/2004

OTHER PUBLICATIONS

Chaby R. Lipopolysaccharide binding Molecules. CMLS Cellular and Molecular Life Sciences 61:1697-1713, 2004.*
Kramer R. et al. Lipopolysaccharide Regions Involved in the Activation of *E. coli* Outer Membrane Protease OmpT. European J Biochem 269:1746-1752, 2002.*
Goh, Y. et al. A Novel Fluorescent Protein Based Biosensor for Gram Negative Bacteria. Applied and Environmental Microbiology 68(12)6343-6352, Dec. 2002.*
Handbook of Proteolytic Enzymes, Second Edition, vol. 1, Chapter 61, "Omptin", Edited by Alan J. Barrett, Neil D. Rawlings and J. Fred Woessner, Elsevier Academic Press, 2004.
R. A. Kramer et al., Lipopolysaccharide regions involved in the activation of *Escherichia coli* outer membrane protease OmpT, Eur. J. Biochem. 269, 1746-1752 (2002).
Guideline on Validation of the Limulus Amebocyte Lysate Test as an End-Product Endotoxin Test for Human and Animal Parenteral Drugs, Biological Products, and Medical Devices, Dec. 1987, Prepared by Center for Drug Evaluation/Biological Evaluation and Research/Center for Devices and Radiological Health/Center for Veterinary Medicine.
R. Chaby, "Lipopolysaccharide-binding molecules: transporters, blockers and sensors", CMLS Cellular and Molecular Life Sciences, 61(2004) 1697-1713.
R. A. Kramer et al., "In vitro folding, purification and characterization of *Escherichia coli* outer membrane protease OmpT", Eur. J. Biochem. 267(2000) 885-893.
R. A. Kramer, "Outer membrane protease OmpT of *Escherichia coli*: functional and structural characterization", Chapters 1-7 (Thesis), 2001, University of Utrecht, Utrecht Netherlands (ISBN 90-393-2791-2) Note: Scanned in two parts.
K. Brandenburg et al., "Investigation into the interaction of the bacterial protease OmpT with outer membrane lipids and biological activity of OmpT:lipopolysaccharide complexes", Eur. Biophys. J. (2005)34: 28-41.
AAMI (Association for the Advancement of Medical Instrumentation), American National Standards Institute, Inc., "Bacterial endotoxins—Test methodologies, routine monitoring, and alternatives to batch testing", ANSI/AAMI ST72:2002.
K. Sugimura et al., "Purification, Characterization, and Primary Structure of *Escherichia coli* Protease VII with Specificity for Paired Basic Residues: Identity of Protease VII and OmpT", J. of Bacteriology, vol. 170, No. 12, 5625-5632, Dec. 1988.

* cited by examiner

*Primary Examiner* — Ralph Gitomer
(74) *Attorney, Agent, or Firm* — Browdy and Neimark, P.L.L.C.

(57) ABSTRACT

The present invention relates to a method for detecting the presence or non-presence of an endotoxin, characterized in that an OmpT protein is brought into contact with a sample suspected of containing an endotoxin and the protease activity of the OmpT protein is assayed. It also relates to a method for detecting early onset of septicaemia using the inventive method and a kit for performing the method.

8 Claims, 2 Drawing Sheets

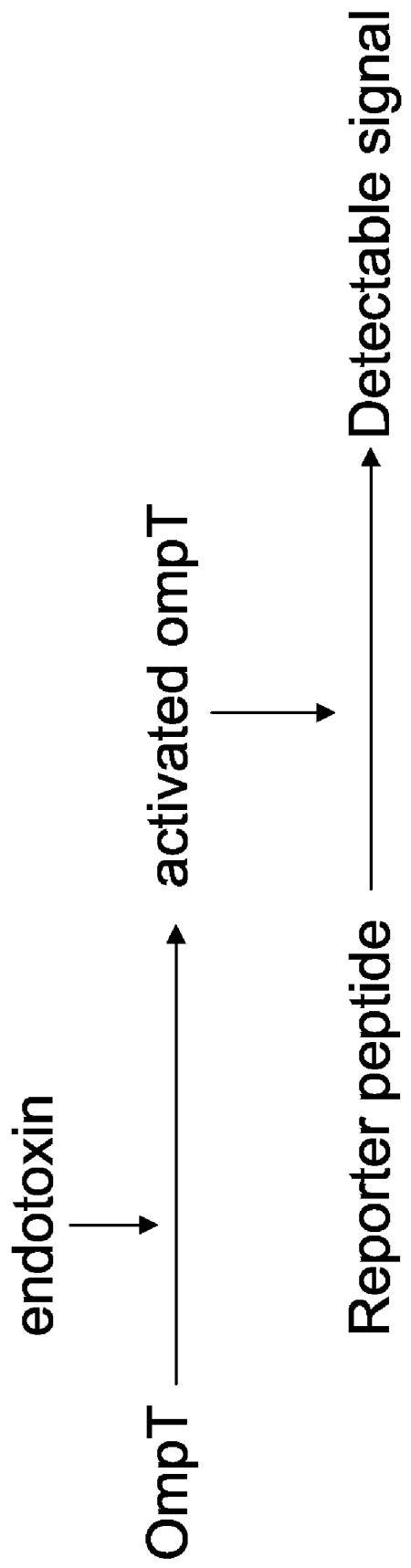

ENDOTOXIN ANALYSIS

FIELD OF THE INVENTION

The present invention relates to the field of endotoxin analysis

BACKGROUND OF THE INVENTION

Endotoxin Analysis

Endotoxins are lipopolysaccharides (LPS) found in the outer membrane of the cell-wall of Gram-negative bacteria. Endotoxins comprise a lipid part, called lipid A, a core oligosaccharide making up the backbone of the macromolecule, and an O-antigen consisting of a variety of repeating oligosaccharide residues. It is lipid A that confers toxicity to the molecule.

Endotoxins are powerful pyrogens and cause i.a. fever, meningitis and a rapid fall in blood pressure if introduced into blood or tissues of the body. Components of the outer membrane such as endotoxins are released into the environment when Gram-negative bacteria lyse or divide, resulting in contamination of the environment. This contamination is difficult to prevent because endotoxins are ubiquitous, stable and small enough to pass through conventional sterilizing filters.

It is therefore of great importance to test pharmaceutical preparations and medical equipment that will be introduced into the body of a patient for endotoxin contamination. The method presently preferred to detect endotoxins is based on a lysate of amebocytes from the blood of the horseshoe crab, *Limulus polyphemus*. An alternative method is the rabbit pyrogenicity test, wherein a sample suspected of containing endotoxin is injected into a rabbit while monitoring the rabbit's body temperature.

The *Limulus* Amebocyte Lysate (LAL) method comprise four reaction steps, see FIG. 1. It is based on a cascade of enzyme activation steps terminating in the cleavage of the peptide coagulogen. This results in insoluble cleavage products, coagulin which coalesce by ionic interaction. If a sufficient amount of coagulin forms, turbidity appears followed by a gel-clot. The clotting enzyme that cleaves coagulogen also cleaves other peptides comprising a cleavage site similar to that in coagulogen. This has been used to construct peptides with such a cleavage site and a chromophore, paranitroanilide (pNA). Cleavage of this peptide results in the release of pNA which is yellow and absorbs light at 405 nm. The release of pNA can thus be measured in a chromogenic assay. The LAL method is further described in FDA guidelines (1987) and ANSI/AAMI standard ST72:2002.

A major disadvantage of the LAL method is that a number of substances interfere with the method in its different steps and care must be taken to keep such substances from interfering. Examples of such substances are heparin, yeast and mould cell wall material and cellulosic material.

Another disadvantage of the LAL method is that the components of the lysate degrade quickly and the lysate consequently has a limited shelf life. Producing the lysate also includes the drawing of blood from live crabs. About 10-15% of the crabs do not survive this treatment and it is estimated that 20 000-37 500 crabs die each year following this treatment. Furthermore, as any product isolated from nature, the exact composition of the lysate differs between batches, which affects the reproducibility of the method.

Chaby, R. reviewed a number of LPS-binding molecules in Cellular and Molecular Life Sciences, vol. 61 (2004) pp 1697-1713. The ongoing attempts to find endotoxin detection reagents were acknowledged by the author. But even though Chaby notes that the enzymatic activity of OmpT requires the ligation of LPS, it is not suggested by this author that this property of OmpT can be used in an assay for detection of endotoxin.

There is thus a great need for a quicker, cheaper, more reliable and animal friendly method for endotoxin analysis. There is also a need for more stable reagents for use in such a method.

Outer Membrane Protease T

The outer membrane protease T, OmpT, is a component of the outer membrane of *E. coli*. It has given name to the serine peptidase family S18, omptin. OmpT has been suggested to be involved in urinary tract disease since ompT genes were found in clinical isolates of *E. coli*. It has also been suggested that OmpT participates in the degradation of antimicrobial peptides secreted by epithelial cells from the urinary tract. However, the general biological function of OmpT remains to be elucidated. It has recently been found to be dependent on lipopolysaccharides for its activity (Kramer, R. A (2000), Brandenburg, K. et al (2005)). These publications do however not disclose that LPS may be detected in a sample by measuring the OmpT activity.

SUMMARY OF THE INVENTION

The present invention is based on the realization that the activation of OmpT by lipopolysaccharides can be used in a new and improved analytical method for detection of endotoxins.

In a first aspect, the invention relates to a method for detecting the presence of an endotoxin, wherein a pure OmpT protein is brought into contact with a sample suspected of containing an endotoxin and the protease activity of the OmpT protein is assayed. Said activity is indicative of the presence of an endotoxin in the sample, and lack of activity is indicative of non-presence of endotoxin.

In a preferred embodiment the activity of the OmpT protein is assayed by the addition of a reporter peptide that may be cleaved by active OmpT and on such cleavage generates a detectable signal. The reporter peptide preferably generates a colour or fluorescent signal.

In a further preferred embodiment the OmpT protein is native OmpT purified from *E. coli*, in vitro-synthesized, or recombinantly produced. The recombinant host may be either a bacterium, such as *E. coli*, or a host organism not producing endotoxins, such as *Pichia pastoris*.

The samples may derive from patients, medical equipment, water, air, soil or dust or any other material suspected of being contaminated with endotoxins.

In a second aspect, the invention relates to a diagnostic method for diagnosing septicaemia.

In a third aspect, the invention relates to a kit comprising reagents for performing the method according to the first and the second aspect.

BRIEF DESCRIPTION OF THE DRAWINGS

FIG. 2 is a flow chart showing the analytical method according to the present invention.

DEFINITIONS

Figure 1:
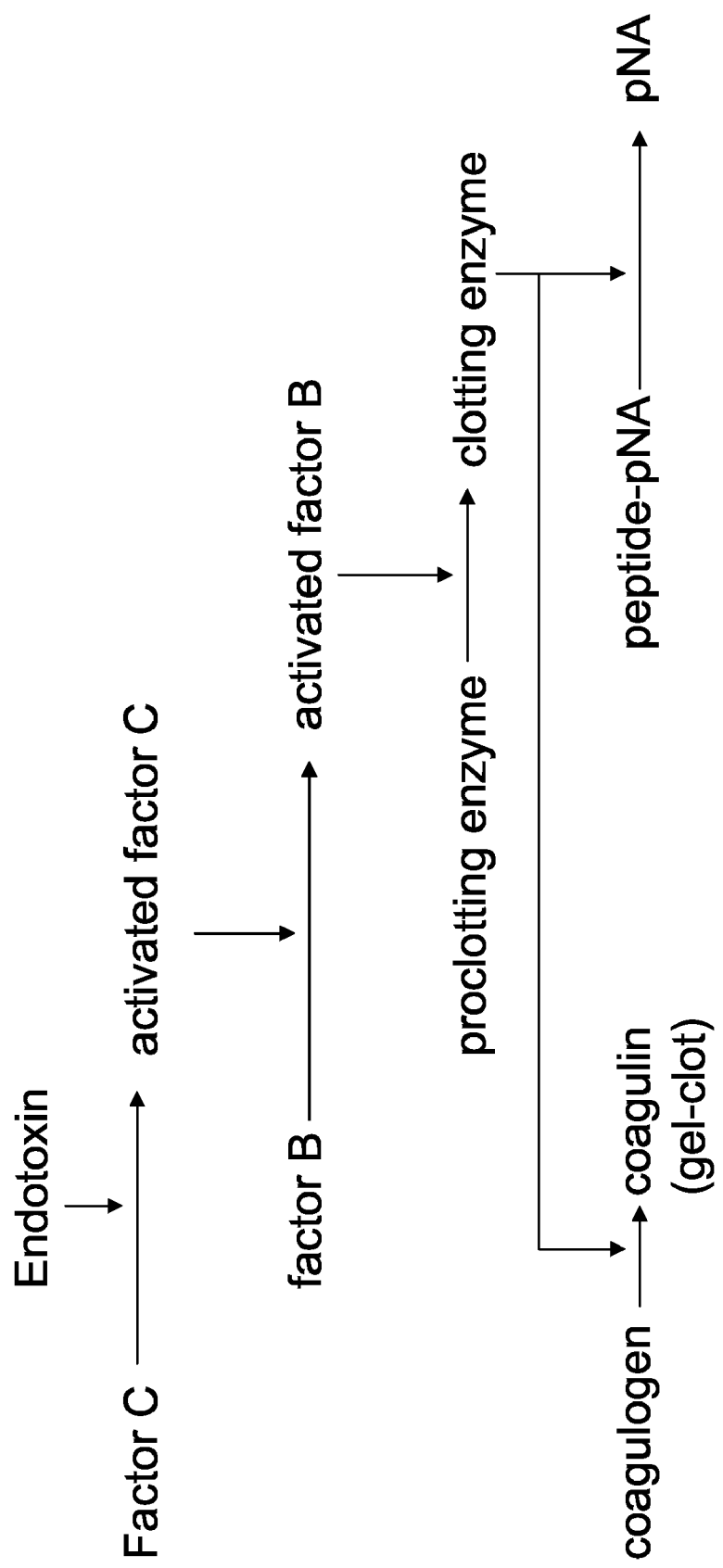
FIG. 1 is a flow chart of a known endotoxin analysis with *Limulus* Amebocyte Lysate.

All terms used in this application are intended to have the meaning usually given to them by a person skilled in the pertinent art. However, a few terms are defined below for the sake of clarity.

Endotoxin refer to a lipopolysaccharide molecule being naturally present in the outer membrane of Gram-negative bacteria and showing toxicity in mammals. In this application the term "lipopolysaccharide" or "LPS" is used when referring to the physicochemical properties of the molecule, such as its ability to activate OmpT, and the term "endotoxin" is used when referring to the molecule as a health hazard. The term "endotoxin" should also be construed as including parts of said lipopolysaccharide, e.g. lipid A, showing said toxic properties.

pNA means para-nitroanilide.
IAA means indole-3-acetic acid
Abz means o-aminobenzoyl.

A pure OmpT protein should be construed as meaning a preparation of OmpT protein essentially free of components affecting its protease activity. Particularly, a pure OmpT protein is free of LPS.

A reporter peptide as used in this document is a peptide, polypeptide or protein that upon contact with active OmpT generates a detectable signal.

DETAILED DESCRIPTION OF THE INVENTION

The method according to the present invention is based on the interaction of purified OmpT and lipopolysaccharides of Gram-negative bacteria. The Outer Membrane Protease OmpT is a protease having a unique substrate specificity, cleaving peptides between two consecutive basic amino acids. The OmpT protein is also dependent on the presence of lipopolysaccharides for its activity. The method according to the invention thus in its broadest aspect relates to a method wherein purified OmpT is brought into contact with a sample suspected of containing an endotoxin and the activity of the OmpT protein is assayed.

The physical embodiment of the method can be in any of a number of formats. The OmpT protein may be immobilized on a solid support, such as a microtiter plate, or it may be in a solution.

The activity assay for OmpT is preferably done by adding a peptide, hereinafter called "reporter peptide", comprising an OmpT cleavage site and analysing whether this reporter peptide is cleaved by OmpT or not. The reporter peptide can be added to the OmpT protein or to the sample before, after or at the same time as the sample and the OmpT protein are brought into contact. The reporter peptide should be constructed so that it contains an OmpT cleavage site and a signal group that generates a detectable signal when the reporter peptide is cleaved by OmpT. A reaction scheme for this activity assay is given in FIG. 2.

Presently known or suspected OmpT cleavage sites are Arg-Arg, Lys-Lys, Lys-Arg, Arg-Lys, Arg-Ser, Arg-Val, Arg-Met, Arg-Ala, Lys-Ala, Lys-Gln and Lys-Thr (Kramer, A. (2001)).

The signal group could be any group that generates a detectable signal. If necessary, the reporter peptide should comprise a quenching group that quench the signal from the signal group until the peptide is cleaved. Presently preferred are chromogenic and fluorescent groups, such as p-nitroanilide or o-aminobenzoyl.

One example of a reporter peptide is Abz-Ala-Arg-Arg-Ala-Tyr($NO_2$)—$NH_2$. Excitation of the Abz-group with light at 325 nm results in a fluorescence signal with an emission maximum at 430 nm. This fluorescence is quenched by the Tyr($NO_2$)-group until the groups are separated by cleavage of the reporter peptide.

Another example of a reporter peptide is IAA-Arg-Arg-pNA. Cleavage of this peptide by OmpT results in IAA-Arg, which may then be cleaved by aminopeptidase M to yield IAA. IAA can be detected spectrophotometrically at 405 nm.

The OmpT protein may be derived from any available source as long as it has the desired properties, i.e. it should be activated by the presence of LPS and it should possess a specific protease activity. Preferably, the OmpT protein is OmpT from *E. coli* (UniProt Knowledgebase accession number P09169), but it is probable that any homologue of this protein from other Gram-negative bacteria could be useful in the present invention. The OmpT protein may be isolated from an organism naturally producing OmpT or it may be recombinantly produced, preferably in organisms not producing LPS such as *Pichia pastoris*. It could also be synthesized in vitro by cell-free synthesis.

The sample to be analyzed may comprise substances interfering with the analysis. One group of such interfering substances is proteases cleaving the reporter peptide, giving a positive result in the assay irrespective of the presence of endotoxin. In one embodiment of the invention, such proteases are inhibited in the assay. They may be inhibited by physical means, e.g. by heating, changing the pH or the charge, or by chemical means, e.g. addition of protease inhibitors. Such inhibitors should however not inhibit the OmpT protease activity.

The sample to be analyzed may be of many different origins. It may be derived from an individual, e.g. a donor of blood, plasma or some other organ, or a patient undergoing autologous blood transfusion. It may also be derived from a medical device intended for contact with body fluids or internal organs of a patient, such as surgical instruments and implantable devices. It may be derived from a pharmaceutical composition. Furthermore, it may be derived from air, dust, soil or solid materials suspected of contaminating or being contaminated by an environment, such as a building damaged by damp.

In one aspect, the invention relates to the detection of endotoxin as an early marker for the onset of septicaemia. In this aspect, a blood sample from a patient suspected of being at risk of developing septicaemia is subjected to the method according to the first aspect.

In a further aspect, the invention relates to a kit comprising the necessary parts for carrying out the method for detecting endotoxin. Such a kit preferably includes a preparation of pure OmpT protein and a reporter peptide. It may further comprise instruments for taking samples, such as swabs, spatulas, syringes or air filters, washing liquids for sampling devices, buffer solutions for diluting samples and/or vials for performing the assay.

EXAMPLES

Production of OmpT Protease from *E. coli*

(purification protocol below is a modification following a method described by Sugimura and Nishihara (1988) with modification described by Kramer A (2001)).

Cultivation: For purification of native OmpT from the outer membrane of native *E. coli,* cells expressing wild-type OmpT and its signal sequence are cultivated in a suitable size bioreactor to the amounts necessary to achieve the desired amount of OmpT and under conditions optimal for OmpT expression with respect to pH and temperature. Cultivation can be performed in complex as well as salts medium with glucose addition and during batch or fedbatch conditions.

Harvest: The cell culture is harvested by centrifugation (2500 rmp, 15 min) and the pellet is then washed with buffer A (50 mM Tris/HCl, pH 7.5) and recentrifuged. The pellet is then suspended in buffer A.

Cell disruption: Cells are thereafter disrupted by shear forces through the use of French press or other cell homogenising methods. Non-disrupted cells are withdrawn by centrifugation (1000 g, 10 min). Whole cell membrane fractions are collected by centrifugation (36000 g for 40 minutes).

Purification: The pellet is washed with buffer A and recentrifuged (36000 g, 40 min). The pellet is washed with 0.1% sarcosyl in buffer A for 1 h at 4° C. during shaking to separate the inner and the outer membrane. The pellet is collected by ultracentrifugation (36000 g, 40 min). OmpT is extracted from the membrane with TritonX-100 and 5 mM EDTA in buffer A for 1 h at room temperature on a shake board. After ultracentrifugation (36000 g, 40 min), the supernatant is applied to a DEAE-cellulose column equilibrated by buffer B (10 mM DodMe$_2$NPrSO$_3$, 20 mM Tris/HCl, pH 7.5). Absorbed proteins are eluted by a linear gradient of NaCl to 0.5 M in 700 mL of buffer B. Fractions are analysed by SDS-PAGE and the activity by a colorimetric assay. Fractions including pure OmpT are pooled, dialysed against buffer B and stored in −20° C.

Production of Recombinant OmpT

The gene encoding *E. coli* OmpT protease is isolated by PCR using a set of primers in a standard PCR amplification using *E. coli* chromosomal DNA as template. Cloning of the resulting PCR product into a suitable expression vector is performed. In this vector the OmpT gene is either unfused or fused to a suitable affinity partner for enhancing possibilities of efficient purification and/or to support the possibility of covalent coupling of the OmpT protein to a surface. The protein can then be produced in a variety of hosts which might be chosen on basis of not naturally producing any contaminating LPS. If the protein has been overexpressed in *E. coli* it can be produced in the cytosol, in the periplasm of *E. coli* or in the outer membrane, the two latter by use of a signal sequence. Several signals can be used also from other organisms. In order to maximise the production in the outer membrane the native signal is used and to enhance the production in the periplasm outer membrane signals are avoided and periplasmic protein sequences are instead used (e.g. the signal used for transport of MalE or even OmpA which has a track record of not interfering with the outer membrane).

Purification without affinity fusion partner: Purification of a cytoplasmic located protein fraction is either done by harvest of the whole cell or by selective removal of the outer membrane and the periplasm. For purification parts of the protocol for extraction of native OmpT above is used. For periplasmic localisation of the product the same strategy is followed but the outer membrane and periplasmic fraction is collected.

For enrichment of OmpT in the membrane the method suggested for native OmpT purification is followed.

Purification using affinity partner: If an affinity partner is used the whole cell extract can be added to a purification column e.g. using principles of expanded bed adsorption (EBA) where the column is suited for adsorption of the fusion tag used.

Production of a Reporter Peptide Substrate for OmpT Activity

Detection of the proteolytic activity of OmpT is preferably done by FRET based analysis. The reporter peptide may be produced by conventional solid phase peptide chemistry in a process leading to coupling of fluorophore and quencher groups positioned site-specifically to the proteolytic cleavage site. Proteolytic cleavage sites are chosen from those susceptible to cleavage by OmpT. Presently known cleavage sites are Arg-Arg, Lys-Lys, Lys-Arg, Arg-Lys, Arg-Ser, Arg-Val, Arg-Met, Arg-Ala, Lys-Ala, Lys-Gln and Lys-Thr. Analysis is performed by HPLC analysis/MS.

The reporter peptide can also be purchased commercially (e.g. from Bachem, Switzerland)

Endotoxin Analysis Using a Surface-Immobilized OmpT Protease

Recombinant or native OmpT protease is suspended in a suitable buffer allowing adsorption onto a plastic surface (e.g. polystyrene). Alternatively, using affinity fusion-tagged OmpT protease protein, such immobilization can be achieved via biospecific interaction such as covalently coupled via EDC/NHS activated surfaces to primary amines or other suitable coupling chemistry. After the surface deposit is achieved the LPS sample is added which activates the OmpT protease. Finally, the reporter peptide is added which leads to OmpT cleavage of the reporter peptide in case endotoxin is present in the sample. Detection and quantification of the reporter signal is done by analysis of the spectral analysis which can be either individually of each sample or in a scanning multiparallel fashion. The analysis is performed at optimal pH and temperature, which parameters are readily adjusted by the person skilled in the art.

Endotoxin Analysis Using OmpT Protease in Solution

Recombinant or native OmpT protease is suspended in a suitable buffer with the sample suspected of containing endotoxin, allowing activation of the protease function. This is followed by addition of the reporter peptide which leads to OmpT cleavage of the reporter peptide in case endotoxin is present in the sample.

Detection of the reporter signal is done as above. The analysis is performed at optimal pH and temperature, which parameters are readily adjusted by the person skilled in the art.

REFERENCES

American National Standards Institute (2002), ANSI/AAMI ST72:2002, Bacterial endotoxins—Test methodologies, routine monitoring, and alternatives to batch testing Brandenburg, K. (2005) et al, Eur. Biophys. J., vol. 34, pp. 28-41

Chaby, R. (2004), Cellular and Molecular Life Sciences, vol. 61 pp 1697-1713

Food and Drug Administration (1987), Guideline on validation of the *Limulus* Amebocyte Lysate test as an end-product endotoxin test for human and animal parenteral drugs, biological products, and medical devices.

Kramer, R. A. (2000), et al, Eur. J. Biochem., vol 267, pp 885-893

Kramer A (2001) PhD thesis University of Utrecht, NL, ISBN 90-393-2791-2

Sugimura and Nishihara (1988), Purification, characterisation and primary structure of *Escherichia coli* protease VII with specificity for paired basic residues: the identity of protease VII and OmpT. J Bact 170:5625-5632

The invention claimed is:

1. Method for detecting the presence or absence of an endotoxin, which comprises providing a sample suspected of containing an endotoxin, but for which the presence or absence of the endotoxin is not initially known, bringing an OmpT protein having a protease activity in the presence of an endotoxin into contact with said sample, assaying the protease activity of the OmpT protein, and correlating the protease activity with the presence or absence of the endotoxin, wherein protease activity indicates presence of the endotoxin and absence of protease activity indicates absence of the endotoxin.

2. Method according to claim 1, wherein the protease activity is assayed by adding a reporter peptide comprising an OmpT cleavage site, said reporter peptide giving a detectable signal on cleavage.

3. Method according to claim 1, wherein the OmpT protein is purified OmpT from *E. coli*.

4. Method according to claim 1, wherein the OmpT protein is recombinantly produced or in vitro-synthesized.

5. Method according to claim 1, wherein the sample is selected from the group consisting of patient samples, pharmaceutical compositions, medical equipment, water, air, soil and dust.

6. A method for detecting onset of septicaemia, wherein a blood, plasma or serum sample from a patient is subjected to the method according to claim 1, and the onset of septicaemia is correlated with the presence of said endotoxin.

7. The method of claim 1, in which all of the endotoxin in the sample is endogenous to said sample.

8. Method for detecting the amount of an endotoxin, which comprises providing a sample suspected of containing an endotoxin, but for which the amount of the endotoxin in the sample is not initially known, bringing an OmpT protein having a protease activity in the presence of an endotoxin into contact with said sample, assaying the level of protease activity of the OmpT protein, and correlating the level of protease activity with the amount of the endotoxin.

* * * * *